(12) United States Patent
Pillarisetti et al.

(10) Patent No.: US 7,273,712 B2
(45) Date of Patent: Sep. 25, 2007

(54) METHODS AND COMPOSITIONS FOR DETECTING COMPOUNDS THAT MODULATE INFLAMMATORY RESPONSES

(75) Inventors: Sivaram Pillarisetti, Norcross, GA (US); Shianlen Cahoon, Atlanta, GA (US); Uday Saxena, Atlanta, GA (US)

(73) Assignee: Reddy US Therapeutics, Inc., Norcross, GA (US)

( * ) Notice: Subject to any disclaimer, the term of this patent is extended or adjusted under 35 U.S.C. 154(b) by 337 days.

(21) Appl. No.: 10/026,335

(22) Filed: Dec. 21, 2001

(65) Prior Publication Data

US 2002/0086282 A1 Jul. 4, 2002

Related U.S. Application Data

(60) Provisional application No. 60/259,306, filed on Dec. 29, 2000.

(51) Int. Cl.
*C12Q 1/02* (2006.01)
*G01N 33/53* (2006.01)
(52) U.S. Cl. .............. 435/7.24; 435/7.21; 435/29; 435/377
(58) Field of Classification Search .............. 435/7.21, 435/7.24, 29, 377
See application file for complete search history.

(56) References Cited

U.S. PATENT DOCUMENTS

| | | | | |
|---|---|---|---|---|
| 5,846,959 A | * | 12/1998 | Medford et al. | 514/165 |
| 6,340,459 B1 | * | 1/2002 | Yellin et al. | 424/154.1 |
| 6,900,041 B2 | * | 5/2005 | Cahoon et al. | 435/194 |
| 7,173,032 B2 | * | 2/2007 | Timmer et al. | 514/245 |
| 2002/0086282 A1 | * | 7/2002 | Pillarisetti et al. | 435/4 |

FOREIGN PATENT DOCUMENTS

WO WO97/20063 * 6/1997

OTHER PUBLICATIONS

Cruse et al, Illustrated Dictionary of Immunology, CRC Press, 1995, pp. 302-303.*
Brownlee, M., et al., "Aminoguanidine prevents diabetes-induced arterial wall protein cross-linking", *Science*, vol. 232, pp. 1629-1632, (1986).
Brownlee, M., et al., "Nonenzymatic glycosylation and the pathogenesis of diabetic complications", *Annuals of Internal Medicine*, vol. 101, pp. 527-537, (1984).
Cohen, M.P., et al., "Role of amadori-modified nonenzymatically glycated serum proteins in the pathogenesis of diabetic nephropathy", *Journal of the American Society of Nephrology*, vol. 7, No. 2, pp. 183-190.
Eitner, F., et al., "Role of interleukin-6 in mediating mesangial cell proliferation and matrix production *in vivo*", *Kidney International*, vol. 51, pp. 69-78 (1997).
Hofmann, M. A., et al., "RAGE mediates a novel proinflammatory axis: A central cell surface receptor for S100/Calgranulin polypeptides",*Cell*, vol. 97, pp. 889-901 (1999).
Horii, Y., et al., "Role of interleukin-6 in the progression of mesangial proliferative glomerulonephritis", *Kidney International*, vol. 43, Suppl. 39, pp. S-71-S-75, (1993).
Huber, S.A., et al., "Interleukin-6 exacerbates early atherosclerosis in mice", *Arterioscler. Thromb. Vasc. Biol.*, vol. 19, pp. 2364-2367.
Kado, S., et al., "Circulating levels of interleukin-6, its soluble receptor and interleukin-6/interleukin-6 receptor complexes in patients with type 2 diabetes mellitus", *Acta. Diabetol.*, vol. 36, pp. 67-72, (1999).
Lander, H. M., et al., "Activation of the receptor for advanced glycation end products triggers a $p21^{ras}$ -dependent mitogen-activated protein kinase pathway regulated by oxidant stress", *The Journal of Biological Chemistry*, vol. 272, No. 28, pp. 17810-17814 (1997).
Li, Y.M., et al., "Prevention of cardiovascular and renal pathology of aging by the advanced glycation inhibitor aminoguanidine", *Proc. Natl. Acad. Sci.*, vol. 93, pp. 3902-3907 (1996).
Morohoshi, M., et al., "The effect of glucose and advanced glycosylation end products on IL-6 production by human monocytes", *Annals of the New York Academy of Sciences*, vol. 748, pp. 562-570 (1995).
Park, L., et al., "Suppression of accelerated diabetic atherosclerosis by the soluble receptor for advanced glycation endproducts", *Nature Medicine*, vol. 4, No. 9, pp. 1025-1031 (1998).
Piercy, V., et al., "Potential benefit of inhibitors of advanced glycation end products in the progression of type II diabetes: A study with aminoguanidine in C57/BLKsJ diabetic mice", *Metabolism*, vol. 47, No. 12, pp. 1477-1480 (1998).
Saitoh A., et al., "Urinary levels of monocyte chemoattractant protein (MCP)-1 and disease activity in patients with IgA nephropathy", *Journal of Clinical Laboratory Analysis*, vol. 12, pp. 1-5, (1998).
Schmidt, A.M., et al., "Activation of receptor for advanced glycation end products", *Circulation Research*, vol. 84, pp. 489-497 (1999).
Schmidt, A.M., et al., "Advanced glycation endproducts interacting with their endothelial receptor induce expression of vascular cell adhesion molecule-1 (VCAM-1) in cultured human endothelial cells and in mice", *Journal of Clinical Investigation*, vol. 96, pp. 1395-1403 (1995).

(Continued)

Primary Examiner—David A. Saunders
(74) Attorney, Agent, or Firm—Robert S. Thomas (57) ABSTRACT

The present invention relates to compositions and methods for identification and development of compounds or therapeutic agents that treat pathophysiological conditions arising from inflammatory responses. In particular, the present invention is directed to methods for detecting compounds or therapeutic agents that inhibit or block glycated protein produced induction of the signaling-associated inflammatory response in cells. The present invention provides compositions for and methods of treatment of biological conditions including, but not limited to, vascular complications of type I and type II diabetic induced vasculopathies, other vasculopathies, microangiopathies, renal insufficiency, Alzheimer's syndrome, and inflammation-induced diseases such as atherosclerosis.

12 Claims, 3 Drawing Sheets

OTHER PUBLICATIONS

Soulis, T., et al., "Effects of aminoguanidine in preventing experimental diabetic nephropathy are related to the duration of treatment", *Kidney International*, vol. 50, pp. 627-634 (1996).

Taguchi, A., et al., "Blockade of RAGE-amphoterin signalling suppresses tumour growth and metastases", *Nature*, vol. 405, pp. 354-360 (2000).

Takagi, M., et al., "Advanced glycation end products stimulate interleukin-6 production by human bone-derived cells", *Journal of Bone and Mineral Research*, vol. 12, No. 3, pp. 439-446 (1997).

Thornalley, Paul J., "Cell activation by glycated proteins AGE receptors, receptor recognition factors and functional classifcation of AGEs", *Cellular and Molecular Biology*, vol. 44., No. 7, pp. 1013-1023 (1998).

Wada, R., et al., "Only limited effects of aminoguanidine treatment on peripheral nerve function, (Na+, K+)-ATPase activity and thrombomodulin expression in streptozotocin-induced diabetic rats", *Diabetologia*, vol. 42, pp. 743-747 (1999).

Wautier, J.L., et al., "Receptor-mediated endothelial cell dysfunction in diabetic vasculopathy", *J. Clin. Invest.*, vol. 97, No. 1, pp. 238-243 (1996).

Yan, S., et al., "Amyloid-beta peptide-receptor for advanced glycation end product interaction elicits neuronal expression of macrophage-colony stimulating factor: a proinflammatory pathway in Alzheimer disease." *Proc. Natl. Acad. Sci. U.S.A.*, vol. 94, pp. 5296-5301 (1997).

Yang, C.W., et al., "Advanced glycation end products up-regulate gene expression found in diabetic glomerular disease.," *Proc. Natl. Acad. Sci. U. S. A.*, vol. 91, pp. 9436-9440 (1994).

Yano M, et al., "Immunohistochemical localization of glycated protein in diabetic rat kidney" *Diabetes Res. and Clin. Pract.*, vol. 8, pp. 215-219 (1990).

Bian, Z.M., et al., "Glycated Human Serum Albumin Induces IL-8- and MCP-1 Gene Expression in Human Corneal Keratocytes", *Current Eye Research*, vol. 17, pp. 65-72 (1998).

Sengoelge, G., et al., "Endothelial Cell Adhesion Molecule and PMNL Response to Inflammatory Stimuli and AGE-modified Fibronectin", *Kidney International*, vol. 54, No. 5, pp. 1637-1651 (1998).

Schmidt, A.M., et al., "Activation of Receptor for Advanced Glycation End Products", *Circulation Research*, vol. 84, pp. 489-497 (1999).

Marui, N. et al., Vascular Cell Adhesion Molecule-1 (VCAM-1) Gene Transcription and Expression are Regulated through an Antioxidant-sensitive Mechanism in Human Vascular Endothelial Cells, The American Society for Clinical Investigation, Inc., Oct. 1993, vol. 92, 1866-1874.

Schreck, R. et al., Dithiocarbamates as Potent Inhibitors of Nuclear Factor kB Activation in Intact Cells, J. Exp. Med., The Rockefeller University Press, May 1992, vol. 175, 1181-1194.

Neumann, A. et al., Pro-Inflammatory Effects of AGEs: AGE-Induced Transduction in Macrophages, Journal of the American Society of Nephrology, Sep. 2000, 485A, vol. 11, American Society of Nephrology, U.S.A.

\* cited by examiner

METHODS AND COMPOSITIONS FOR DETECTING COMPOUNDS THAT MODULATE INFLAMMATORY RESPONSES

RELATED APPLICATIONS

This Application claims benefit of Provisional Application 60/259,306 filed Dec. 29, 2000. The aforementioned is hereby incorporated by reference in its entirety.

TECHNICAL FIELD

The present invention relates to compositions and methods for identifying compounds that treat pathophysiological conditions arising from inflammatory responses. In particular, the present invention is directed to methods and compositions for treating inflammation and inflammation related diseases, and preferably comprise compounds that inhibit or block glycated protein produced induction of the signaling-associated inflammatory response in endothelial cells.

BACKGROUND OF THE INVENTION

Glycated proteins and advanced glycation end products (AGE) accumulate slowly in vascular and renal tissues with age, and more rapidly in inflammatory disease states. AGE contribute to cellular damage, particularly, diabetic tissue injury, by at least two major mechanisms: modulation of cellular functions through interactions with specific cell surface receptors, and alteration of the extracellular matrix leading to the formation of protein cross-links. Studies suggest that glycated protein and AGE interactions with cells may promote inflammatory processes and oxidative cellular injury. Diseases where glycated protein and AGE accumulation is a suspected etiological factor include vascular complications of diabetes, ventricular hypertrophy, atherosclerosis, angiopathy, myocarditis, nephritis, arthritis, glomerulonephritis, microangiopathies, renal insufficiency and Alzheimer's disease.

The exact mechanisms by which high plasma glucose, as seen in diabetes, causes microvascular damage are not completely understood. One potential mechanism by which hyperglycemia can be linked to microangiopathies is through the process of non-enzymatic glycation of critical proteins (1-3). Non-enzymatic glycation, i.e. the linking of proteins with glucose, leads to the formation of glycated proteins. The first step in this glycation pathway involves the non-enzymatic condensation of glucose with free amino groups in the protein, primarily the epsilon-amino groups of lysine residues, forming the Amadori adducts. These early glycation products can undergo further reactions such as rearrangements, dehydration and condensations to form irreversible advanced glycation end products (AGE). AGE are a highly reactive group of molecules whose interaction with specific cell-surface receptors, are thought to lead to pathogenic outcomes. Accumulation of glycated proteins is found in the basement membrane of patients with diabetes and is thought to be involved in the development of diabetic nephropathy and retinopathy (4,5). Inhibitors of AGE formation, such as aminoguanidine, prevent development of diabetes complications, including diabetic retinopathy (6-8).

The best characterized AGE receptor is RAGE, receptor for AGE (3). Several in vitro and in vivo studies have shown that blocking RAGE either by antibodies or by adding a soluble form of the receptor inhibits diabetic vasculopathy including diabetic atherosclerosis (9-11). Apart from AGE, RAGE appears to mediate the binding of several other ligands that are involved in normal physiology as well as pathology (12,13). Thus, merely blocking RAGE might have other unintended consequences. Moreover, since blocking RAGE would lead to accumulation of AGE in circulation, the long-term effects of blocking RAGE are unknown and may be more harmful than the pathology sought to be prevented.

There are currently no efficient methods for determining compounds effective for the inhibition of AGE or glycated protein accumulation. What is needed are methods and compositions for detecting compounds that can be used to interfere with the production of glycated proteins or AGE. Such detection methods and compositions need to be high throughput and capable of determining effective compounds easily.

SUMMARY OF THE INVENTION

The present invention is directed to methods and compositions for the detection of compounds that are effective in the inhibition of AGE and glycated protein inflammation. The methods of the present invention comprise addition of compounds to assays that measure inflammation created by AGE or glycated protein accumulation and determination of the effect of the compounds, such as inhibition of inflammation by the compounds. Such assays are rapid and accurate tests for glycated protein-induced inflammation and the inhibition of such inflammation by potential therapeutic compounds.

Preferred embodiments of the present invention include methods and compositions for the measurement of endothelial cytokines induced by glycated protein-induced inflammation. More preferred assays measure determinants such as, but not limited to, NF-κB, IL-1β (interleukin 1β), IL-11 (interleukin 11), m-CSF (macrophage colony stimulating factor), fibrinogen, TNF-α (tumor necrosis factor α), adhesion molecules, selectins, VCAM-1 (Vascular Cell Adhesion Molecule-1), CRP (C-reactive protein), and PAI-1 (plasminogen activator inhibitor-1). Most preferred cytokines include IL-6 and monocyte chemoattractant protein 1 (MCP-1). These assays provide for rapid and accurate high throughput screening of molecules that block or inhibit glycated protein-induced inflammation. The identification of these effector molecules and compounds leads to effective therapies for treatment of pathologies resulting from the biological effects of AGE and glycated protein accumulations and interactions.

The present invention also comprises compositions comprising the compounds identified by the assays as having a desired activity. The compositions have utility in treatment of cells, tissues or whole organisms. Such compositions are formulated for administration in an effective amount for treatment of conditions such as biological conditions including, but not limited to, vascular complications of type I and type II diabetic induced vasculopathies, other vasculopathies, microangiopathies, renal insufficiency, Alzheimer's syndrome, and inflammation-induced diseases including, but not limited to, atherosclerosis. The compositions may comprise pharmacutical adjuncts that are needed for administration of the compound or compounds with the desired activity.

DETAILED DESCRIPTION OF THE INVENTION

The present invention is directed to methods and compositions for detecting compounds or molecules that have specific biological effects and that may be useful as therapeutic agents. In particular, the present invention is directed to methods and compositions for detecting compounds or molecules that affect inflammation. More particularly, the present invention is directed to methods and compositions for detecting compounds or molecules that are effective in inhibiting inflammation caused by the accumulation or presence of glycated proteins or AGE. The present invention also provides compositions for and methods of treatment for biological conditions including, but not limited to, vascular complications of type I and type II diabetic-induced vasculopathies, other vasculopathies, angiopathy, myocarditis nephritis, arthritis, coronary artery disease, microangiopathies, renal insufficiency, Alzheimer's syndrome, and inflammation induced diseases including, but not limited to, atherosclerosis.

The present invention is useful in determining which compounds or molecules are active in inhibiting inflammation or cell activation by glycated proteins or AGE. AGE increases lipoprotein oxidizability and atherogenicity. Not wishing to be bound by any particular theory, it is thought that AGE binds to matrix proteins, induces synthesis of IL-1, TNFα, VCAM-1, Heme oxygenase, insulin like growth factor and IL-6, and activates NF-κB. Pharmacological inhibition of AGE-induced cell activation may provide the basis for therapeutic intervention in many diseases, most notably in diabetic complications and Alzheimer's disease.

Useful methods to block AGE effects are determining inhibitors that block AGE induced signaling. The sequence of signaling events leading to inflammation are unclear. A way to overcome this problem is to screen for compounds that block AGE-induced up-regulation of inflammatory molecules. The present invention comprises methods and compositions that enable one to screen for such compounds or molecules.

Preferred embodiments of the present invention comprise methods for screening for compounds that block glycated protein-induced inflammation. More preferred embodiments comprise methods for screening for inhibitory compounds or molecules that comprise addition of such compounds to assays for measuring inflammatory determinants, such as inflammatory cytokines, and determining the inhibitory effects of the compound. Most preferred embodiments comprise methods comprising assays wherein glycated albumin stimulates endothelial production of determinants, particularly determinants of inflammation such as IL-6, MCP-1, IL1-β, TNF-α, CRP, PAI-1, VCAM-1, ICAM-1, selectins, and adhesion molecules. The endothelial cell is important in inflammation reactions, and the methods and compositions described herein provide for high throughput screening of molecules that block glycated protein-induced inflammation.

As used herein, the term "compound" includes both the singular and the plural, and includes any single entity or combined entities that have activity that can be measured in the assays of the present invention. Such entities include, but are not limited to, chemical elements, molecules, compounds, mixtures, emulsions, chemotherapeutic agents, pharmacological agents, hormones, antibodies, growth factors, cellular factors, nucleic acids, proteins, peptides, peptidomimetics, nucleotides, carbohydrates, and combinations, fragments, analogs or derivatives of such entities.

In the assays of the present invention, the compound initially has unknown activity, effect or effects. The activity of the compound is unknown, in that the compound's effects in the assays of the present invention are not yet determined. The compound may have many other known activities, and may be a compound that has other therapeutic uses.

Stimulatory agent, as used herein, is the component of the assay that stimulates the cells of the assay to respond in a predetermined or known manner. The stimulatory agent can be a chemical compound or molecule or a biological factor. In a most preferred embodiment, the stimulatory agent is a glycated protein, most preferably, glycated human serum albumin (G-HSA). Glycated protein, as used herein, includes proteins linked to glucose, either enzymatically or non-enzymatically, primarily by condensation of free epsilon-amino groups in the protein with glucose, forming Amadori adducts. Furthermore, glycated protein, as used herein, includes not only proteins containing these initial glycation products, but also glycation products resulting from further reactions such as rearrangements, dehydration, and condensations that form irreversible advanced glycation end products. This embodiment is not limiting and any agent that causes the cells or components of the assay to respond in a measurable manner is contemplated by the present invention.

Enhanced formation and accumulation of glycated proteins and AGE are thought to play a major role in the pathogenesis of diabetic complications, and atherosclerosis, leading to the development of a range of diabetic complications including nephropathy, retinopathy and neuropathy (1-3). There is ample in vivo evidence that suggests that diabetes-related complications can be reduced by 1) preventing glycation of proteins (6-8) 2) by breaking the cross-links in glycated proteins (22) or 3) by blocking glycated protein interaction with receptors (10,11). Despite the importance of AGE in the pathogenesis of diabetic microangiopathies, and vasculopathies, there are no currently available medications known to block AGE formation.

Aminoguanidine, which prevents AGE formation, is actively pursued as a therapy for diabetic vasculopathy (8-10). However it is not clear whether this drug would affect normal glucose metabolism or glycosylation of proteins. Moreover, some studies show that although aminoguanidine reduces AGE formation, it did not inhibit glomerular basement thickness in diabetic rats nor improved endothelial function (18,19).

In addition to the AGE formation inhibitors, AGE crosslink breakers are also actively pursued as a therapy for vasculopathy. N-Phenacylthiazolium bromide (PTB) is a prototype AGE cross-link breaker that reacts with and cleaves covalent AGE-derived protein cross-links. Although PTB reduced AGE accumulation, it did not prevent vascular permeability.

Inhibition of reactions with receptors of AGE are an alternative approach to treatment of related pathologies. RAGE, a known receptor for AGE, is a possible therapeutic target. Blocking RAGE also inhibited AGE-induced inflammation. However, because of the multiple functions of RAGE and possible long term side effects of accumulated AGE in plasma, this method is not currently pursued in humans. Using the methods and compositions of the present invention, more specific inhibitory compounds can be determined.

Though not wishing to be bound by any particular theory, it is theorized that the present invention utilizes the end point measurement in AGE-induced inflammation. Endothelium is the target organ of damage in diabetes (20,21). Up-regulation of molecules involved in endothelial inflammation, such as IL-6 and monocyte chemoattractant protein-1 (MCP-1) leads to endothelial dysfunction and vasculopathy (21). An overall approach to the understanding and treatment of diabetes and its complications is to interfere in the regulation of genes, such as these two.

The present invention comprises methods and compositions for measuring the activity of compounds. Such methods comprise assays for specific activity of biological components involved in a known cellular response. The assays provide a measurable response in which the activity of the compounds is determined. This response can be measured by methods known to those skilled in the art, preferably in an ELISA. A preferred embodiment of the present invention comprises measurement of the effects of compounds on an inflammatory response by cells to the presence of a stimulating agent.

In another embodiment of the present invention, a composition suspected of affecting inflammation is added to cells which are then treated with a stimulatory agent. The stimulatory agent may also be added prior to or simultaneously with the composition suspected of affecting inflammation. The cells respond by producing specific determinants of inflammation. The amount of these determinants can be measured by methods known to those skilled in the art and compared to the amount of determinants produced by cells which are treated with the stimulating agent and not the composition suspected of affecting inflammation. The compound may have a stimulating effect, an inhibitory effect, a stabilizing effect, or no effect at all.

A further embodiment of the present invention comprises an assay comprising endothelial cells that are stimulated by the addition of a glycated protein, the stimulating agent. The endothelial cells respond by producing specific cytokines. The amount of cytokines produced are determined by measurement protocols known to those skilled in the art. Compounds having unknown effects are added to the same assay conditions and the production of cytokines is measured. From the comparison of the assay without the compound with the assay with the compound, the biological effect of the compound can be determined. The compound may have an inhibitory effect, a stimulatory effect, a stabilizing effect or no effect at all.

Another preferred embodiment of the present invention comprises measurement of the effects of compounds on the accumulation of AGE or glycated proteins by measuring the response of cells.

In another embodiment of the present invention, a composition suspected of affecting the accumulation of AGE or glycated protein is added to cells which are also treated with a glycated protein. The glycated protein can be added prior to, subsequently to or simultaneously with the composition suspected of affecting accumulation of AGE or glycated protein. The cells respond by producing specific determinants of AGE or glycated protein accumulation. The amount of these determinants can be measured by methods known to those skilled in the art and compared to the amount of determinants produced by cells which are treated with the stimulating agent and not the composition suspected of affecting AGE or glycated protein accumulation. The compound may have a stimulating effect, an inhibitory effect, a stabilizing effect, or no effect at all.

Most preferred embodiments of the present invention comprise methods for determining the activity of compounds using assays. The preferred assays comprise endothelial cells that are stimulated in an inflammatory response by the presence of the glycated protein, glycated human serum albumin. The endothelial cells of the preferred embodiment produce cytokines. A preferred method comprises measurement of the amount of the cytokine IL-6 and another preferred embodiment comprises measurement of the amount of the cytokine MCP-1. Preferably, the amount of cytokine produced is determined using immunological methods, more preferably using ELISA assays. The methods of the present invention are not limited by the type of assay used to measure the amount of cytokine produced, and any methods known to those skilled in the art and later developed can be used to measure the amount of cytokines produced in response to the stimulating agent and to the compound having unknown activity.

IL-6 is a pro-inflammatory cytokine that is known to play a key role in the pathogenesis of diabetes and atherosclerosis (23). IL-6 also promotes the growth of renal mesangial cells thus contributing to nephropathy (24). The serum IL-6 level in diabetic subjects was significantly higher than in normal healthy controls (3.48+/−3.29 pg/ml vs 0.784+/−0.90 pg/ml, mean +/−SD). In addition the urinary IL-6 level is a good indicator of diabetic nephropathy. Serum IL-6 is useful in the evaluation of atherosclerosis and nephropathy.

MCP-1, another pro-inflammatory cytokine is found highly expressed in human atherosclerotic lesions and postulated to play a central role in monocyte recruitment into the arterial wall and developing lesions. Recent results show that MCP-1 is also a key pathogenic molecule in diabetic nephropathy (25). The levels of urinary MCP-1 in patients with the advanced stage were significantly higher than those in patients with the mild stage of the disease, or in healthy controls. The measurement of urinary MCP-1 is useful in evaluating the degree of renal injuries and/or prognosis in patients with nephropathy.

Glycated albumin stimulates endothelial production of IL-6 and MCP-1. The effects on IL-6 are comparable to that of TNFα, a known inducer of IL-6. Because of the well established role of these cytokines in vascular diseases, screening for compounds that block AGE-induction of these cytokines provides a novel approach for identifying therapeutic agents that block AGE-induced inflammation in vivo.

In a preferred embodiment, once the baseline response to the stimulating agent for the production of cytokines by the endothelial cells is established, thus comprising the control levels for the screening assay, the methods comprise addition of compounds having unknown activities. The effect of the compound on the baseline response is determined by comparing the amount of cytokine produced in the presence of the stimulating agent and the amount of cytokine produced in the presence of the stimulating agent and the compound having unknown activity. In a preferred method, compounds that have inhibitory effects on the inflammation of the cells in the presence of G-HSA are then selected for further testing for use as therapeutic agents. One or more compounds may be added to the screening assay. Combinations or mixtures of compounds can be added. Different amounts and formulations of the compounds are added to determine the effects on the screening assay. The screening assay may also be used to determine stimulatory compounds or compounds that have no effects in the assay.

The present invention also comprises compositions comprising the compounds identified by the methods as having a desired activity. The compositions have utility in treatment of cells, tissues or whole organisms. Such compositions are formulated for administration in an effective amount for treatment of conditions such as biological conditions including, but not limited to, vascular complications of type I and type II diabetic induced vasculopathies, other vasculopathies, microangiopathies, renal insufficiency, Alzheimer's syndrome, and inflammation-induced diseases including, but not limited to, atherosclerosis. The compositions may comprise pharmacutical adjuncts that are needed for administration of the compound or compounds with the desired activity.

The compositions of the present invention may be administered through routes of administration that include, but are not limited to, oral, buccal, nasal, aerosol, topical, transdermal, injectable, slow release, controlled release, iontophoresis, sonophoresis, and other delivery devices and methods. Injectable methods include, but are not limited to, intravenous, intramuscular, intraperitoneal, intraspinal, intrathecal, intracerebroventricular, intraarterial, subcutaneous and intranasal routes.

The compositions for treating the pathologies by the present invention can further include a pharmaceutically acceptable carrier. The compositions can also include other medicinal agents, pharmaceutical agents, carriers, adjuvants diluents and other pharmaceutical preparations known to those skilled in the art. These agents are known to those skilled in the art and are generally described as being biologically inactive and can be administered to patients without causing deleterious interactions with the active agent. Examples of carriers or excipients for oral administration include corn starch, lactose, magnesium stearate, microcrystalline cellulose and stearic acid, povidone, dibasic calcium phosphate and sodium starch glycolate. Any carrier suitable for the desired administration route is contemplated by the present invention.

It is to be understood that this invention is not limited to the particular formulations, process steps, and materials disclosed herein as such formulations, process steps, and materials may vary somewhat. It is also to be understood that the terminology employed herein is used for the purpose of describing particular embodiments only and is not intended to be limiting since the scope of the present invention will be limited only by the appended claims and equivalents thereof.

All patents and patent applications disclosed herein are hereby incorporated by reference in their entirety. All references listed or cited herein are incorporated by reference in their entirety.

The foregoing description includes the best presently contemplated mode of carrying out the invention. This description is made for the purpose of illustrating the general principles of the inventions and should not be taken in a limiting sense. This invention is further illustrated by the following examples, which are not to be construed in any way as imposing limitations upon the scope thereof. On the contrary, it is to be clearly understood that resort may be had to various other embodiments, modifications, and equivalents thereof, which, after reading the description herein, may suggest themselves to those skilled in the art without departing from the spirit of the present invention.

EXAMPLES

Example 1

AGE-Induced Inflammatory Response Determined by IL-6 ELISA:

Human aortic (HAEC) and microvascular (HMVEC) endothelial cells (Clonetics) were cultured and subcultured according to manufacturer in growth medium (Clonetics): basal medium containing hEGF, hydrocortisone, VEGF, HFGF-B (with heparin), long R3-IGF-1, ascorbic acid, gentamicin/amphotericin and 5% FBS. These cell were allowed to reach >90% confluency before being subjected to experimental treatments. G-HSA was from US Biologicals. Tumor necrosis factor $\alpha$ (TNF$\alpha$) was from R&D Systems.

HMVEC were treated with control medium or medium containing 100 ng/ml TNF$\alpha$ or 300 µg/ml G-HSA for 24 hrs. All treatments and controls were carried out in serum free media containing 0.2% albumin. Following treatment, cell media were collected and used for an IL-6 ELISA.

The IL-6 ELISA was carried out using human IL-6 DuoSet ELISA development kit as described by manufacturer (R&D Systems). Mouse anti-human IL-6 was used as the capture antibody (2 µg/ml) and biotinylated goat anti-human IL6 (200 ng/ml) was used as the detection antibody. The culture media were incubated with capture antibody for 2 h at room temperature in 96-well plates. The wells were washed three times with wash buffer (0.05% Tween-20 in phosphate buffered saline (PBS) pH 7.4) followed by incubation with detection antibody for 2 h at room temperature. Following three washes, the wells were incubated with Streptavidin-HRP for 20 min. Color development was read at 450 nm in a microplate reader.

Figure 1:
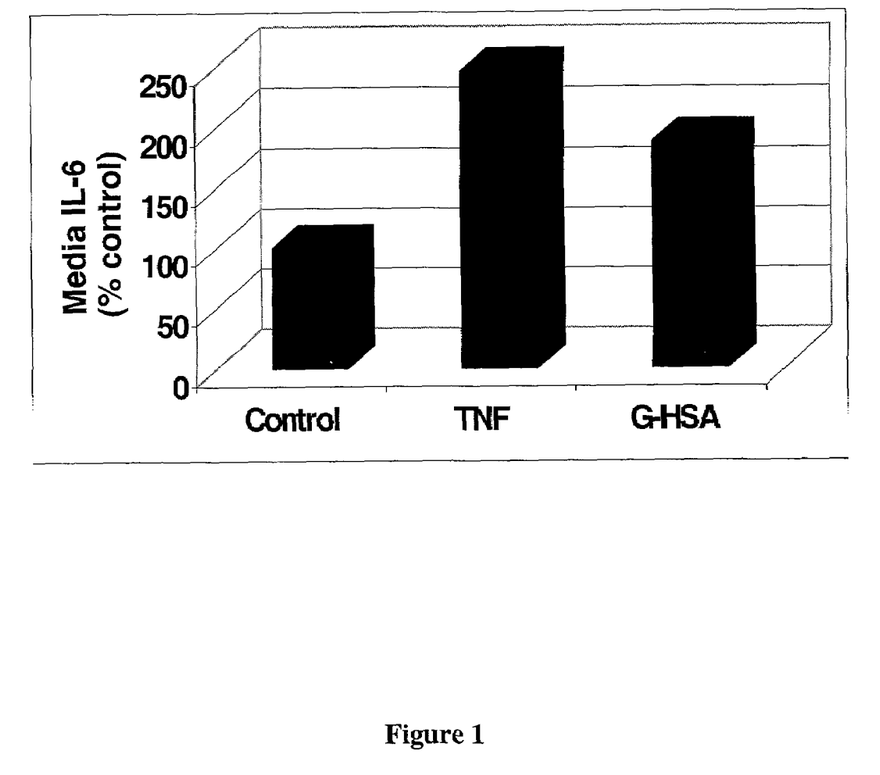
FIG. 1 is a graph showing the effects of glycated human serum albumin (G-HSA) in induction of IL-6 production in endothelial cells.

Endothelial cells under basal conditions secreted about 25-100 pg/ml, of IL-6. Incubation of endothelial cells with TNF$\alpha$, a known inducer of IL-6, induced greater than 2-fold increase in IL-6 secretion by endothelial cells. Similarly, G-HSA increased IL-6 secretion by 87%. These data show that G-HSA induced IL-6 secretion in endothelial cells comparable to TNF$\alpha$. As shown in FIG. 1, incubation with TNF$\alpha$ and G-HSA led to an 147% and 87% increase in IL-6 secretion respectively.

Example 2

AGE-Induced Inflammatory Response Determined by MCP-1 ELISA:

HAEC and HMVEC (Clonetics) were cultured and subcultured according to manufacturer in growth medium (Clonetics): basal medium containing hEGF, hydrocortisone, VEGF, HFGF-B (with heparin), long R3-IGF-1, ascorbic acid, gentamicin/amphotericin and 5% FBS. These cells were allowed to reach >90% confluency before being subjected to experimental treatments. G-HSA was from US Biologicals. TNF$\alpha$ was from R&D Systems.

Cells were treated with control medium or medium containing 100 ng/ml TNF$\alpha$ or 300 µg/ml G-HSA for 24 hrs. All treatments and controls were carried out in serum free media containing 0.2% albumin. Following treatment, media were collected and used for the MCP-1 ELISA.

MCP-1 ELISA was carried out using a DuoSet ELISA Development System for Human MCP-1 as described by the manufacturer (R&D Systems). 2 ug/ml of mouse anti-human MCP-1 was used as the capture antibody and 100 ng/ml biotinylated goat anti-human MCP-1 was used as the detection antibody. The culture media were incubated with capture antibody for 2 h at room temperature in 96-well plates.

The wells were washed three times with wash buffer (0.05% Tween-20 in phosphate buffered saline (PBS) pH 7.4) followed by incubation with detection antibody for 2 h at room temperature. Color development was read at 450 nm in a microplate reader.

Figure 2:
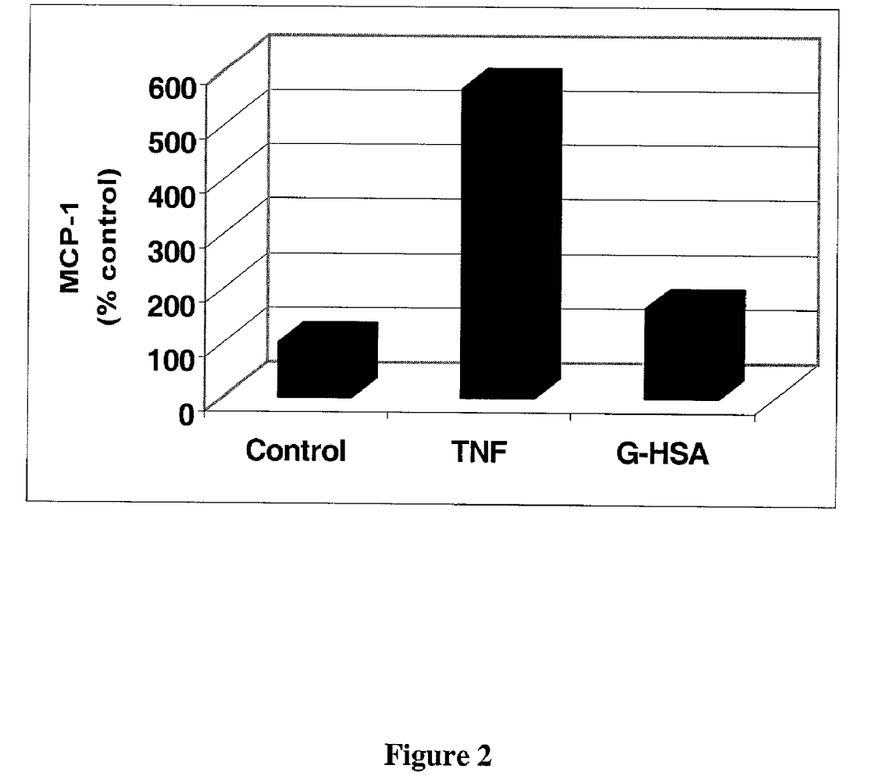
FIG. 2 is a graph showing the effects of G-HSA in induction MCP-1 production in endothelial cells.

The effects of G-HSA on endothelial MCP-1 are shown in FIG. 2. Endothelial cells under control conditions produced about 400 pg/ml MCP-1. Incubation with TNFα and G-HSA led to 540% and 65% increase in MCP-1 secretion respectively.

Example 3

Figure 3:
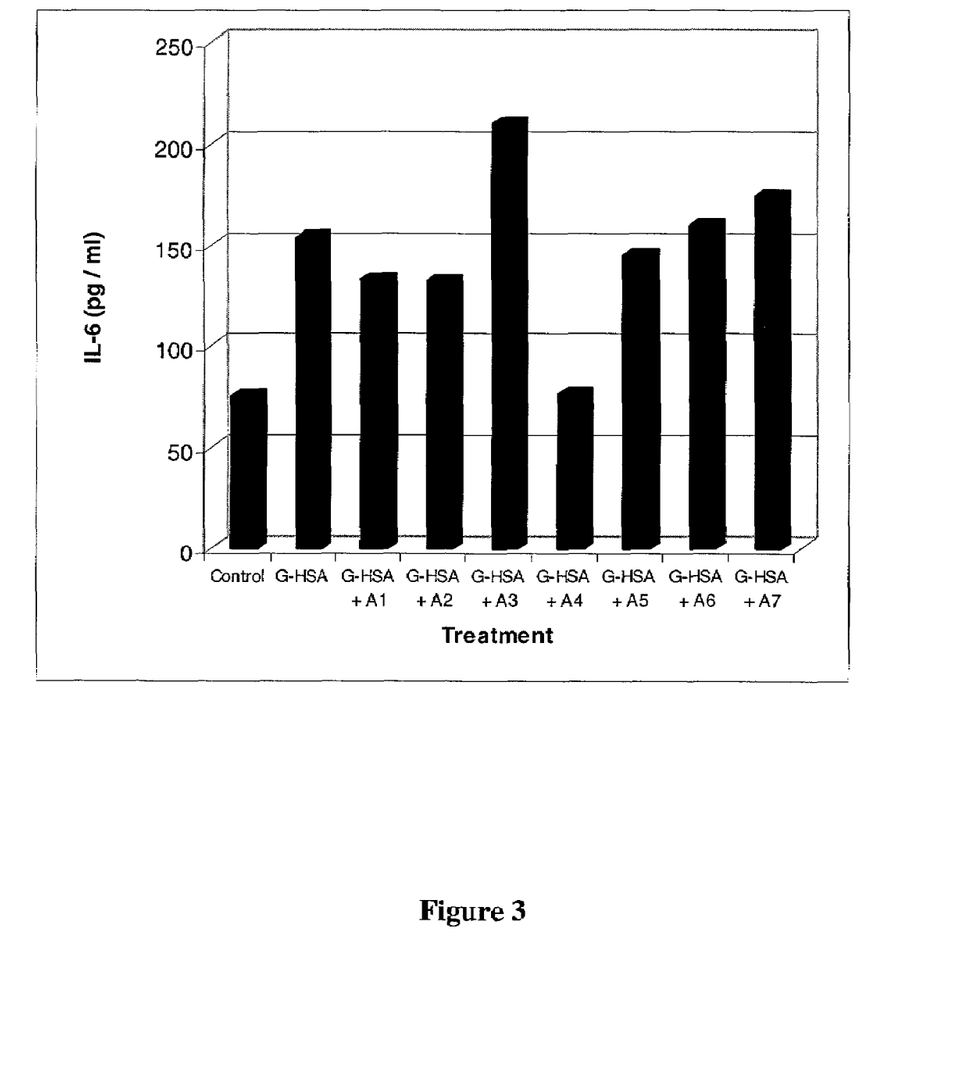
FIG. 3 is a graph showing results obtained from screening a collection of compounds to identify those compounds that block G-HSA produced induction of IL-6 in endothelial cells.

High-Throughput Screening of Compounds that Block AGE Produced Induction of Inflammatory Response Determined by IL-6 ELISA:

Endothelial cells were incubated in control media or media containing 300 μg/ml G-HSA or media containing 300 μg/ml G-HSA and 10 μM of a test compound. Representative data for a series of test compounds (A1-A7) from this collection are shown in FIG. 3. Compared to untreated cells (74 pg/ml), cells incubated with G-HSA had a two fold increase in IL-6 secretion (150 pg/ml). Of the compounds shown herein, one (A4) was able to block G-HSA induced secretion of IL-6. IL-6 secretion was normalized to near basal levels by compound A4. Although the results in FIG. 3 are only for seven compounds, the method of the present invention is designed for high-throughput screening such that greater than 250 compounds can be screened in duplicate by one person in less than one week.

REFERENCES

1. Brownlee M, et al. Nonenzymatic glycosylation and the pathogenesis of diabetic complications. Ann Intern Med 1984; 101:527-537.
2. Yang C W, et al. Advanced glycation end products up-regulate gene expression found in diabetic glomerular disease. Proc Natl. Acad. Sci. U. S. 1994 91:9436-40.
3. Schmidt A M, et al. Activation of receptor for advanced glycation end products: a mechanism for chronic vascular dysfunction in diabetic vasculopathy and atherosclerosis. Circ Res. 1999 84:489-97.
4. Yano M, et al. Immunohistochemical localization of glycated protein in diabetic rat kidney. Diabetes Res Clin Pract. 1990 8:215-9.
5. Cohen M P, et al. Role of Amadori-modified nonenzymatically glycated serum proteins in the pathogenesis of diabetic nephropathy. J Am Soc Nephrol. 1996 7:183-90.
6. Brownlee M, et al. Aminoguanidine prevents diabetes-induced arterial wall protein cross-linking. Science 232: 1629-1632, 1986.
7. Li Y M, et al. Prevention of cardiovascular and renal pathology of aging by the advanced glycation inhibitor aminoguanidine. Proc Natl Acad Sci U S A. 1996 93:3902-7.
8. Piercy V, et al. Potential benefit of inhibitors of advanced glycation end products in the progression of type II diabetes: a study with aminoguanidine in C57/BLKsJ diabetic mice. Metabolism. 1998 47:1477-80.
9. Wautier J L, et al. Receptor-mediated endothelial cell dysfunction in diabetic vasculopathy. Soluble receptor for advanced glycation end products blocks hyperpermeability in diabetic rats. J Clin Invest. 1996 97:238-43.
10. Schmidt AM, et al. Advanced glycation end products interacting with their endothelial receptor induce expression of vascular cell adhesion molecule-1 (VCAM-1) in cultured human endothelial cells and in mice. A potential mechanism for the accelerated vasculopathy of diabetes. J Clin Invest. 1995 96:1395-403.
11. Park L, et al. Suppression of accelerated diabetic atherosclerosis by the soluble receptor for advanced glycation endproducts. Nat Med. 1998 4:1025-31.
12. Hofmann M A, et al. RAGE mediates a novel proinflammatory axis: a central cell surface receptor for S100/calgranulin polypeptides. Cell. 1999 97:889-901.
13. Du Yan S, et al. Amyloid-beta peptide-receptor for advanced glycation end product interaction elicits neuronal expression of macrophage-colony stimulating factor: a proinflammatory pathway in Alzheimer disease. Proc Natl Acad Sci U. S. 1997 94:5296-301.
14. Lander H M, et al. Activation of the receptor for advanced glycation end products triggers a p21(ras)-dependent mitogen-activated protein kinase pathway regulated by oxidant stress. J Biol Chem. 1997 272: 17810-4.
15. Thornalley P J. Cell activation by glycated proteins. AGE receptors, receptor recognition factors and functional classification of AGEs. Cell Mol Biol. (Noisy-le-grand). 1998 44:1013-23.
16. Morohoshi M, et al. The effect of glucose and advanced glycosylation end products on IL-6 production by human monocytes. Ann N Y Acad Sci. 1995 748:562-70.
17. Takagi M, et al. Advanced glycation endproducts stimulate interleukin-6 production by human bone-derived cells. J Bone Miner Res. 1997 12:439-46.
18. Wada R, et al. Only limited effects of aminoguanidine treatment on peripheral nerve function, (Na+,K+)-ATPase activity and thrombomodulin expression in streptozotocin-induced diabetic rats. Diabetologia. 1999 42:743-7.
19. Soulis T, et al. Effects of aminoguanidine in preventing experimental diabetic nephropathy are related to the duration of treatment. Kidney Int. 1996 50:627-34.
20. Laight D W, et al. Endothelial cell dysfunction and the pathogenesis of diabetic macroangiopathy. Diabetes Metab Res Rev. 15: 274-82 (1999).
21. Stehouwer C D, et al. Endothelial dysfunction and pathogenesis of diabetic angiopathy. Cardiovasc. Res. 34:55-68 (1997).
22. Horii Y, et al. Role of interleukin-6 in the progression of mesangial proliferative glomerulonephritis. Kidney Int Suppl. 1993 39:S71-5.
23. Huber S A, et al. Interleukin-6 exacerbates early atherosclerosis in mice. Arterioscler Thromb Vasc Biol. 1999 19:2364-7.
24. Kado S, et al. Circulating levels of interleukin-6, its soluble receptor and interleukin-6/interleukin-6 receptor complexes in patients with type 2 diabetes mellitus. Acta Diabetol. 1999 36:67-72.
25. Eitner F, et al. Role of interleukin-6 in mediating mesangial cell proliferation and matrix production in vivo. Kidney Int. 1997 51:69-78.
26. Saitoh A, Suzuki Y, Takeda M, Kubota K, Itoh K, Tomino Y. Urinary levels of monocyte chemoattractant protein (MCP)-1 and disease activity in patients with IgA nephropathy. J Clin Lab Anal. 1998 12:1-5.

What is claimed is:

1. A method for detecting a composition that affects inflammation, the method comprising:

a) adding the composition to a first cell culture, wherein the composition comprises a component with an unknown effect on inflammation;
b) adding a glycated protein for inducing production of a determinant of inflammation to the first cell culture and a second cell culture;
c) measuring an amount respectively from the first cell culture and the second cell culture of a produced determinant of inflammation, the first and second cell cultures respectively being endothelial cells, wherein the determinant of inflammation is selected from the group consisting of NF-κB, IL-1, IL-11, TNF-α, ICAM-1, or PAI-1; and
d) comparing the amount of the determinant from the first cell culture to the amount of determinant from the second cell culture to determine whether the composition has a stimulating effect, an inhibitory effect, or no effect on the inflammation.

2. The method of claim 1, wherein the component is a chemical element, a molecule, a compound, a mixture, an emulsion, a chemotherapeutic agent, a pharmacological agent, a hormone, an antibody, a growth factor, a cellular factor, a nucleic acid, a protein, a peptide, a peptidomimetic, a nucleotide, a carbohydrate, or combinations, fragments, analogs or derivatives of such components.

3. The method of claim 1, wherein the determinant of inflammation is selected from the group consisting of IL-1, TNF-α, or PAI-1.

4. The method of claim 1, wherein the glycated protein is G-HSA or AGE.

5. The method of claim 1, wherein after adding the glycated protein, the cells are cultured for a predetermined amount of time.

6. The method of claim 1, wherein the determinant of inflammation is IL-1, or TNF-α.

7. The method of claim 1, wherein the determinant of inflammation is TNF-α.

8. The method of claim 1, wherein b) adding the glycated protein to the first cell culture precedes a) adding the composition to a first cell culture.

9. The method of claim 1, wherein a) adding the composition to a first cell culture and b) adding the glycated protein to the first cell culture occur simultaneously.

10. A method for detecting a composition comprising an activity for inhibiting inflammation, the method comprising:
   a) adding to a first cell culture a composition comprising a component with an unknown effect on inflammation;
   b) adding a glycated protein for inducing production of a determinant of inflammation to the first cell culture and to a second cell culture;
   c) measuring an amount respectively from the first cell culture and the second cell culture of a produced determinant of inflammation, the first and second cell cultures respectively comprising endothelial cells, wherein the determinant of inflammation is selected from the group consisting of NF-κB, IL-1, IL-11, TNF-α, ICAM-1, or PAI-1; and
   d) comparing the amount of the determinant from the first cell culture to the amount of determinant from the second cell culture to determine whether the composition comprises the activity for inhibiting the inflammation.

11. The method of claim 10, wherein the determinant of inflammation is selected from the group consisting of IL-1, TNF-α, or PAI-1.

12. The method of claim 10, wherein the glycated protein is G-HSA or AGE.

* * * * *